United States Patent [19]

Ueno

[11] Patent Number: 5,206,224

[45] Date of Patent: Apr. 27, 1993

[54] TREATMENT OF MALE HORMONE RELATED DISEASES BY CYCLODEXTRINS AND THEIR DERIVATIVES

[75] Inventor: Ryuji Ueno, Hyogo, Japan

[73] Assignee: Kabushikikaisha Ueno Seiyaku Oyo Kenkyujo, Osaka, Japan

[21] Appl. No.: 599,582

[22] Filed: Oct. 18, 1990

[30] Foreign Application Priority Data

Oct. 18, 1989 [JP] Japan ................................ 1-274424
Nov. 15, 1989 [JP] Japan ................................ 1-298090

[51] Int. Cl.$^5$ .................... A61K 31/715; A61K 31/72
[52] U.S. Cl. ........................................ 514/58; 536/103
[58] Field of Search .......................... 514/58; 536/103

[56] References Cited

U.S. PATENT DOCUMENTS

| | | | |
|---|---|---|---|
| 4,258,180 | 3/1981 | Lewis et al. | 536/122 |
| 4,727,064 | 2/1988 | Pitha | 514/58 |
| 4,877,774 | 10/1989 | Pitha et al. | 514/58 |
| 4,877,778 | 10/1989 | Carpenter et al. | 536/103 |
| 5,089,482 | 2/1992 | Hermens et al. | 514/58 |

FOREIGN PATENT DOCUMENTS 293537 12/1988 European Pat. Off.
59-10525 1/1984 Japan.

OTHER PUBLICATIONS

Chemical Abstracts, vol. 98, No. 9, Feb. 28, 1983, abstract No. 98:65432k.
J. Serfozo et al., "Renal Effects of Parenterally Administered Methylated Cyclodextrins on Rabbits", Proc. Int. Symp. Cyclodextrins, 1st 1981 (Pub. 1982), pp. 123-132.
Pharm Tech Japan, 4(2), 59(183)-65(189), (1988).
Separation and Purification Methods, 10(2), 159-237, (1981).
Tetrahedron, 24, 803-821, 1968.
Tetrahedron, 39(9), 1417-1474, 1983.

Primary Examiner—Ronald W. Griffin
Attorney, Agent, or Firm—Sughrue, Mion, Zinn, Macpeak & Seas

[57] ABSTRACT

A method for treatment of diseases having an etiology based on or accompanied by excess male hormone which comprises administering, to a subject in need of such treatment, a cyclodextrin or a derivative thereof in an amount effective in such treatment.

7 Claims, No Drawings

TREATMENT OF MALE HORMONE RELATED DISEASES BY CYCLODEXTRINS AND THEIR DERIVATIVES

BACKGROUND OF THE INVENTION

Field of the Invention

The present invention relates to a method for treatment of diseases having an etiology based on or accompanied by excess male hormone which comprises administering a cyclodextrin or a derivative thereof to a subject.

Among various diseases having an etiology based on or accompanied by excess male hormone, diseases accompanied by enlargement of prostate such as prostatic hypertrophy and prostatic cancer, have conventionally been treated by administration of sex hormones such as estrogens. Since, however, sex hormones have well known side effects, there has been a continuous need of development of a medicament which has not such side effects.

As a result of extensive studies about the properties of non-hormone compounds, the present inventor discovered that cyclodextrin and their derivatives, which have been used only as a complexing agent in the pharmaceutical field, have beneficial action of relieving the disease having an etiology based on or accompanied by excess male hormone, for example action of reducing gain of prostate or testis.

SUMMARY OF THE INVENTION

In a first aspect, the present invention provides a method for treatment of diseases having an etiology based on or accompanied by excess male hormone which comprises administering, to a subject in need of such improvement, a cyclodextrin or a derivative thereof (hereinafter, referred to as the compound used in the invention) in an amount effective in such treatment.

In a second aspect, the present invention provides a method for treatment of enlargement of prostate which comprises administering, to a subject in need of such treatment, a cyclodextrin or a derivative thereof in an amount effective in such treatment.

In a third aspect, the present invention provides a method for treatment of enlargement of testis which comprises administering, to a subject in need of such treatment, a cyclodextrin or a derivative thereof in an amount effective in such treatment.

In a fourth aspect, the present invention provides a use of a cyclodextrin or a derivative thereof for the manufacture of a medicament for treatment of diseases having an etiology based on or accompanied by excess male hormone.

In a fifth aspect, the present invention provides a use of a cyclodextrin or a derivative thereof for the manufacture of a medicament for treatment of enlargement of prostate.

In a sixth aspect, the present invention provides a use of a cyclodextrin or a derivative thereof for the manufacture of a medicament for treatment of enlargement of testis.

In a seventh aspect, the present invention provides a pharmaceutical composition for treatment of diseases having an etiology based on or accompanied by excess male hormone comprising a cyclodextrin or a derivative thereof in association with a pharmaceutically acceptable carrier, diluent or excipient.

In a eighth aspect, the present invention provides a composition for treatment of enlargement of prostate comprising a cyclodextrin or a derivative thereof in associating with a pharmaceutically acceptable carrier, diluent or excipient.

In a ninth aspect, the present invention provides a composition for treatment of enlargement of testis comprising a cyclodextrin or a derivative thereof in association with a pharmaceutically acceptable carrier, diluent or excipient.

DETAILED DESCRIPTION OF THE INVENTION

As used herein, the expression "diseases having an etiology based on or accompanied by excess male hormone" is intended to all kinds of diseases insofar as they are proved or estimated from reliable bases to have at least an etiology based on or accompanied by excess male sex hormone e.g. due to excess secretion or to administration of such hormone. Said diseases include testicular hypertrophy, testicular cancer, prostatic hypertrophy, congenital or aquired adrenologenial syndrome (adrenal virilism following to adrenal hyperplasia, adrenal virilizing tumor which is a tumor having an androgen secreting function, etc.) and also urinary disturbance caused by prostatic hypertrophy (oligurea, ureteral stenosis, ureteral flexion etc.) vesical disturbance (cystitis, vesicoureteral reflux (VUR), etc.). Enlargement of prostate refers to all kinds of prostatic multiplication and prostatic hyperplasia including tumor and thickening, e.g. prostatic hypertrophy (i.e. adenoma of prostate including hypertrophy of bilateral lobes, median lobe, subcervical lobe, commisural, anterior commisural, subtriangle lobe, etc.), prostatic cancer, prostatic sarcoma, etc.

The term "treatment" includes prevention, cure and relief of disease and arrest or relief of development of disease.

The term "cyclodextrin" includes $\alpha$-cyclodextrin, $\beta$-cyclodextrin and $\gamma$-cyclodextrin.

The term "derivatives" used in conjunction with the term cyclodextrin refers to compounds in which at least one atom selected from hydrogen, oxygen or carbon in the cyclodextrin molecule is replaced by an atom or a group of atoms ordinarily present as a substituent in this kind of organic compounds (saccharides). These derivatives include etherified cyclodextrins, branched cyclodextrins, acylated cyclodextrins and sulfur-containing cyclodextrins.

Said etherified cyclodextrins include (lower)alkylcyclodextrins such as methylcyclodextrin, ethylcyclodextrin, propylcyclodextrin, dimethylcyclodextrin, trimethylcyclodextrin etc., (lower)alkenylcyclodextrins, hydroxy(lower)alkylcyclodextrins such as hydroxyethylcyclodextrin, hydroxypropylcyclodextrin etc., (lower)alkoxy(lower)alkylcyclodextrins, aralkylcyclodextrins such as benzylcyclodextrin etc., halo(lower)alkylcyclodextrins such as chloroethylcyclodextrin etc., and cylodextrinepichlorohydrine copolymer and so on. These may be etherified cyclodextrins in which one, two or three hydroxy groups in any of the glucose units of the cyclodextrin molecule are converted into ether.

Said branched cyclodextrins include glucosylcyclodextrin, maltosylcyclodextrin etc.

Said acylated cyclodextrins include (lower)alkanoylcyclodextrins such as formylcyclodextin, acetylcyclodextrin etc., aromatically or heterocyclically acylated cyclodextrins such as benzoylcyclodextrin, nicotinoylcyclodextrin etc.

Said sulfur-containing cyclodextrins include sulfonated cyclodextrins etc.

The derivatives of cyclodextrin include also derivatives in which two or more of derivatizations selected from etherification, branching, acylation and sulfuration are co-existing.

These derivatives are known or can be prepared by a method similar to that for the known derivatives.

While the dosage of cyclodextrin or derivatives thereof will vary depending on age, weight, condition of particular subject, desired therapeutic effect etc., satisfactory effects will generally be obtained with the dosage of 1 $\mu$g/kg to 500 mg/kg, preferably 10 $\mu$g/kg to 50 mg/kg, administered once a day or 2 to 4 divided doses a day or as a sustained form. Administration may be effected by injection etc.

For administration, the compound used in the invention can be given in the form of conventional pharmaceutical preparation which contains said compound, as an active ingredient, in admixture with a pharmaceutically acceptable carrier such as organic or inorganic, solid or liquid excipients suitable for the desired mode of administration such as injection. Such preparation may be in a solid form such as solid from which a solution can be made up before use, etc. or in a liquid form such as solution, emulsion, suspension, etc. Said carrier includes starch, lactose, glucose, sucrose, dextrin cellulose, paraffin, aliphatic glyceride, water, alcohol, acacia etc. The above preparation may also contain auxiliary substance, stabilizer, emulsifier, lubricant, binder, pH-adjuster, isotonic agent and other conventional additives added as necessary.

The present invention is illustrated in more detail by way of the following Examples and Test Examples.

EXAMPLE 1

| Dimethylcyclodextrin | 100 mg |
|---|---|
| Physiological saline | q.s. to 10 ml |

The above ingredients are brought into solution by conventional way to form an injectable solution.

TEST EXAMPLE 1

Male Crj-Wister rats (6 rats per group) intravenously received 5 mg/kg or 25 mg/kg dimethyl-$\alpha$-cyclodextrin [a mixture mainly comprising hexakis(2,6-di-0-methyl)-$\alpha$-cyclodextrin and pentakis[2,6-di-0-methyl)-mono(2,3,6-tri-O-methyl-$\alpha$-cyclodextrin; hereinafter referred to as DMCD] or 25 mg/kg pentakis(2,6-di-0-methyl)-mono(2,3,6-tri0-methyl-$\alpha$-cyclodextrin (purified from commercial DMCD; hereinafter referred to as Compound I, dissolved in 5 ml physiological saline for 2 weeks. Control group received the physiological saline alone.

After the above period, body and testis were weighed for all animals of groups and a weight ratio testis/100 g body was calculated. The results are shown in Table 1. In addition, serum testosteron level was measured. The results are shown in Table 2.

TABLE 1

| Group | Testis (%) | |
|---|---|---|
| | Mean | SD |
| Control | 0.98 | 0.07 |
| DMCD 5 mg/kg | *0.79 | 0.11 |
| DMCD 25 mg/kg | *0.54 | 0.03 |
| Compound I 25 mg/kg | *0.63 | 0.14 |

Dunnet Test: *P < 0.01

TABLE 2

| Group | Testosteron (ng/dl) | |
|---|---|---|
| | Mean | SD |
| Control | 264 | 174 |
| DMCD 5 mg/kg | **104 | 43 |
| Compound I 25 mg/kg | 178 | 100 |

Dunnet Test: **P < 0.05 (one sided)

TEST EXAMPLE 2

Male rats (3 rats per group) were treated as Test Example 1 except that tetrakis(2,6-di-O-methyl)-bis(2,3,6-tri-O-methyl)-$\alpha$-cyclodextrin (purified from DMCD as a mixture; hereinafter referred to as compound II) was used as the test compound. Body and testis were weighed and a weight ratio testis/100 g body was calculated. The results are shown in Table 3. In addition, serum testosteron level was measured. The results are shown in Table 4.

TABLE 3

| Group | Testis (%) | |
|---|---|---|
| | Mean | SD |
| Control | 0.95 | 0.05 |
| Compound II 5 mg/kg | **0.81 | 0.02 |

Dunnet Test: **P < 0.05

TABLE 4

| Group | Teststeron (ng/dl) | |
|---|---|---|
| | Mean | SD |
| Control | 638 | 123 |
| Compound II 5 mg/kg | ***215 | 131 |

Dunnet Test: ***P < 0.05

TEST EXAMPLE 3

Male rats (3 rats per group) were treated as Test Example 1 except that hexakis(2,6-di-0-methyl)-$\alpha$-cyclodextrin (purified from DMCD as a mixture; hereinafter referred to as Compound III) was used as the test compound. Body and testis were weighed and a weight ratio testis/100 g body was calculated. The results are shown in Table 5.

TABLE 5

| Group | Testis (%) | |
|---|---|---|
| | Mean | SD |
| Control | 0.91 | 0.06 |
| Compound III 5 mg/kg | *0.74 | 0.13 |
| Compound III 25 mg/kg | *0.51 | 0.05 |

Dunnet Test: *P < 0.01

TEST EXAMPLE 4

Male rats (12 rats per group) intravenously received 125 mg/kg dimethyl-$\alpha$-cyclodextrin [a mixture mainly comprising hexakis(2,6-di-O-methyl)-$\alpha$-cyclodextrin and pentakis [2,6-di-O-methyl)-mono(2,3,6-tri-O- methyl)-α-cyclodextrin(DMCD)] dissolved in 5 ml physilogical saline for 1 month. Control group received the physiological saline alone.

After the above period, body and prostate were weighed for all animals of groups and a weight ratio testis/100 g body was calculated. The results are shown in Table 6.

TABLE 6

| Group | Prostate (%) | |
| --- | --- | --- |
| | Mean | SD |
| Control | 0.13 | 0.018 |
| Compound II 5 mg/kg | *0.10 | 0.022 |

Dunnet Test: *P < 0.01

The above results indicate that the compounds used in the invention have an action of inhibiting increase in weight of prostate.

What is claimed is:

1. A method for lowering in a patient the level of male hormone which comprises administering to a patient an etherified cyclodextrim in an amount effective for lowering the level of male hormone by said etherified cyclodextrin.

2. A method according to claim 1, in which the patient is a man.

3. A method according to claim 2, in which the etherified cyclodextrin is a dimethycyclodextrin.

4. A method for treatment of enlargement of prostate which comprises administering, to a man in need of such treatment, an etherified cyclodextrin in an amount effective in such treatment.

5. A method according to claim 4, in which the enlargement is in consequence of prostatic hypertrophy.

6. A method for treatment of enlargement of testis which comprises administering, to a man in need of such treatment, an etherified cyclodextrin in an amount effective in such treatment.

7. A method according to claim 6, in which the enlargement is in consequence of testicular hypertrophy.

* * * * *